(12) United States Patent
Cai et al.

(10) Patent No.: US 9,091,666 B2
(45) Date of Patent: Jul. 28, 2015

(54) EXTENDED DEFECT SIZING RANGE FOR WAFER INSPECTION

(75) Inventors: Zhongping Cai, Fremont, CA (US); Yury Yuditsky, Mountain View, CA (US); Anatoly Romanovsky, Palo Alto, CA (US); Alexander Slobodov, San Jose, CA (US)

(73) Assignee: KLA-Tencor Corp., Milpitas, CA (US)

( * ) Notice: Subject to any disclaimer, the term of this patent is extended or adjusted under 35 U.S.C. 154(b) by 668 days.

(21) Appl. No.: 13/369,294

(22) Filed: Feb. 9, 2012

(65) Prior Publication Data

US 2013/0208269 A1   Aug. 15, 2013

(51) Int. Cl.
*G01N 21/88* (2006.01)
*G01N 21/95* (2006.01)

(52) U.S. Cl.
CPC .................................. *G01N 21/9501* (2013.01)

(58) Field of Classification Search
CPC ............. G01N 21/9501; G01N 21/956; H01L 27/14643
USPC ............ 356/237.1–237.5; 438/340, 373, 254, 438/222, 296
See application file for complete search history.

(56) References Cited

U.S. PATENT DOCUMENTS

| 4,302,779 | A   | 11/1981 | Inoue |
| 5,276,520 | A   | 1/1994  | Hawkins et al. |
| 6,489,992 | B2* | 12/2002 | Savoye .......................... 348/340 |
| 8,139,840 | B1* | 3/2012  | Chu et al. ...................... 382/141 |
| 2001/0019361 | A1* | 9/2001 | Savoye .......................... 348/222 |
| 2002/0180970 | A1* | 12/2002 | Hammer et al. ............... 356/330 |
| 2004/0036775 | A1  | 2/2004 | Watson, Jr. et al. |
| 2004/0207836 | A1* | 10/2004 | Chhibber et al. .......... 356/237.4 |
| 2008/0198246 | A1* | 8/2008 | Gardner ......................... 348/254 |
| 2009/0289169 | A1  | 11/2009 | Yang et al. |
| 2010/0051784 | A1  | 3/2010 | Parks |
| 2010/0245640 | A1  | 9/2010 | Bell et al. |

FOREIGN PATENT DOCUMENTS

| KR | 10-2004-0062654 | 7/2004 |
| KR | 10-2004-0063619 | 7/2004 |
| KR | 10-2004-0081607 | 9/2004 |
| WO | 03/046531       | 6/2003 |

OTHER PUBLICATIONS

International Search Report for PCT/US2013/024387 mailed May 27, 2013.

* cited by examiner

*Primary Examiner* — Sang Nguyen
(74) *Attorney, Agent, or Firm* — Ann Marie Mewherter (57) ABSTRACT

Various embodiments for extended defect sizing range for wafer inspection are provided. One inspection system includes an illumination subsystem configured to direct light to the wafer. The system also includes an image sensor configured to detect light scattered from wafer defects and to generate output responsive to the scattered light. The image sensor is also configured to not have an anti-blooming feature such that when a pixel in the image sensor reaches full well capacity, excess charge flows from the pixel to one or more neighboring pixels in the image sensor. The system further includes a computer subsystem configured to detect the defects on the wafer using the output and to determine a size of the defects on the wafer using the output generated by a pixel and any neighboring pixels of the pixel to which the excess charge flows.

21 Claims, 5 Drawing Sheets

| 7 | 6 | 3 | 2 | 4 |
| 5 | 4 | 3 | 7 | 3 |
| 3 | 6 | 4 | 8 | 5 |
| 6 | 3 | 2183 | 4 | 3 |
| 3 | 5 | 3 | 4 | 6 |
| 4 | 3 | 7 | 6 | 3 |
| 3 | 2 | 5 | 8 | 5 |

Fig. 1

| | | | | |
|---|---|---|---|---|
| 7 | 6 | 3 | 2 | 4 |
| 5 | 4 | 3 | 7 | 3 |
| 3 | 6 | 4 | 8 | 5 |
| 6 | 3 | 2183 | 4 | 3 |
| 3 | 5 | 3 | 4 | 6 |
| 4 | 3 | 7 | 6 | 3 |
| 3 | 2 | 5 | 8 | 5 |

*Fig. 2*

| 7 | 6 | 3 | 2 | 4 |
|---|---|---|---|---|
| 5 | 4 | 1013 A | 7 | 3 |
| 3 | 6 | 4095 B | 8 | 5 |
| 6 | 3 | 4095 C | 4 | 3 |
| 3 | 5 | 4095 D | 4 | 6 |
| 4 | 3 | 1057 E | 6 | 3 |
| 3 | 2 | 5 | 8 | 5 |

| 7 | 6 | 3 | 2 | 4 |
|---|---|---|---|---|
| 5 | 4 | 1013 | 7 | 3 |
| 3 | 1883 | 4095 | 1895 | 5 |
| 988 | 4095 | 4095 | 4095 | 896 |
| 3 | 1878 | 4095 | 1769 | 6 |
| 4 | 3 | 1057 | 6 | 3 |
| 3 | 2 | 5 | 8 | 5 |

*Fig. 5*

EXTENDED DEFECT SIZING RANGE FOR WAFER INSPECTION

BACKGROUND OF THE INVENTION

1. Field of the Invention

The present invention generally relates to extended defect sizing range for wafer inspection.

2. Description of the Related Art

The following description and examples are not admitted to be prior art by virtue of their inclusion in this section.

Inspection of wafers and other substrates generally involves detecting defects and determining the size of the defects. Some inspection systems are configured to detect defects by detecting the light scattered from wafer defects. In general, defect size can be determined from the quantity of the light scattered from a wafer defect. For example, light scattering is typically proportional to the sixth power of the defect size. Therefore, the light scattering changes dramatically with defect size. As a result, it is difficult to accurately determine defect sizes across a substantially large measurement range with any one inspection system. However, determining defect sizes across a substantially large measurement range would be advantageous for a number of obvious reasons.

Accordingly, it would be advantageous to develop methods and systems for defect size determination that do not have one or more of the disadvantages described above.

SUMMARY OF THE INVENTION

The following description of various embodiments is not to be construed in any way as limiting the subject matter of the appended claims.

An embodiment relates to a system configured to inspect a substrate. The system includes an illumination subsystem configured to direct light to the wafer. The system also includes an image sensor configured to detect light scattered from wafer defects and to generate output responsive to the scattered light. The image sensor is configured to not have an anti-blooming feature such that when a pixel in the image sensor reaches full well capacity, excess charge flows from the pixel to one or more neighboring pixels in the image sensor, in addition, the system includes a computer subsystem configured to detect the defects on the wafer using the output and to determine a size of the defects on the wafer using the output generated by a pixel and any neighboring pixels of the pixel to which the excess charge of the pixel flows. The system may be further configured according to any embodiment(s) described herein.

Another embodiment relates to a method for inspecting a wafer. The method includes directing light to the wafer. The method also includes detecting light scattered from wafer defects and generating output responsive to the scattered light using an image sensor. The image sensor does not have an anti-blooming feature such that when a pixel in the image sensor reaches full well capacity, excess charge flows from the pixel to one or more neighboring pixels in the image sensor. In addition, the method includes detecting the defects on the wafer using the output. The method further includes determining a size of the defects on the wafer using the output generated by a pixel and any neighboring pixels of the pixel to which the excess charge of the pixel flows.

An additional embodiment relates to a computer-implemented method for determining a size of defects on a wafer. The method includes acquiring output of an image sensor included in an inspection system. The output is generated by directing light to the wafer and detecting light scattered from wafer defects. The image sensor is configured to not have an anti-blooming feature such that when a pixel in the image sensor reaches full well capacity, excess charge flows from the pixel to one or more neighboring pixels in the image sensor. The method also includes using a computer system to detect the defects on the wafer using the output and to determine a size of the defects on the wafer using the output generated by a pixel and any neighboring pixels of the pixel to which the excess charge flows.

Each of the steps of each of the embodiments of the methods described above may be further performed as described herein. In addition, each of the embodiments of the methods described above may include any other step(s) of any other method(s) described herein. Furthermore, each of the embodiments of the methods described above may be performed by any of the systems described herein.

BRIEF DESCRIPTION OF IRE DRAWINGS

Further advantages of the present invention will become apparent to those skilled in the art with the benefit of the following detailed description of the preferred embodiments and upon reference to the accompanying drawings in which.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

In general, the embodiments described herein relate to methods and systems for extending the defect sizing range of inspection systems using an image sensor (e.g., a charge coupled device (CCD) or CMOS sensor) blooming calibration. In this manner, the embodiments described herein may be used to increase the sizing range of defect inspection that uses image sensors. One embodiment relates to a system configured to inspect a wafer. As such, the system may also be referred to as an inspection system or a defect inspection system. Although one configuration of a system is described and shown further herein, the system may include any commercially available inspection system or inspection system in development that is modified to include one or more image sensors that are configured as described herein. Examples of such inspection systems include next generation Surfscan tools that are commercially available from KLA-Tencor, Milpitas, Calif. Although embodiments are described herein with respect to defects on wafers, the embodiments can be used to extend the sizing range of any system that includes one or more image sensors such as those described herein and is configured to determine the size of any feature formed on any substrate.

Figure 1:
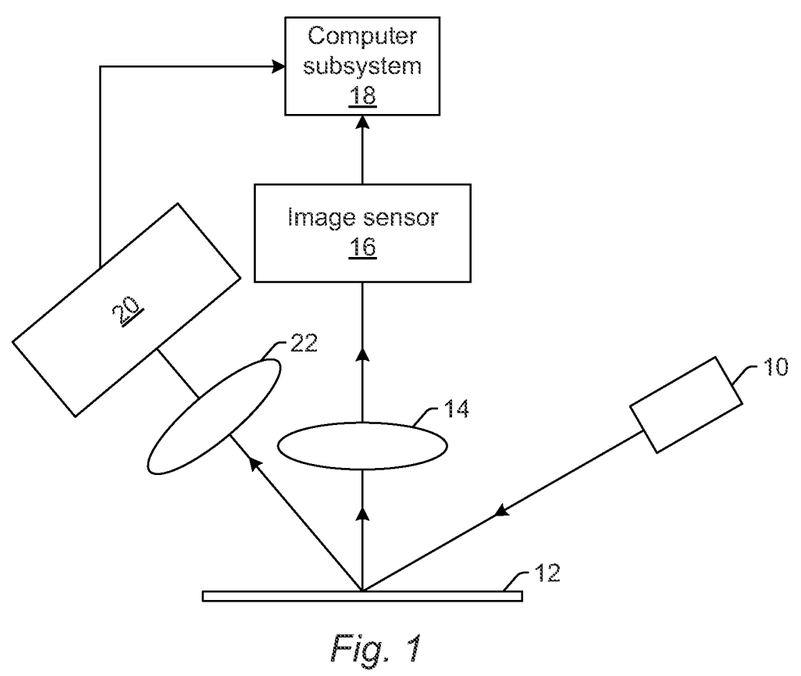
FIG. 1 is a schematic diagram illustrating a side view of one embodiment of a system configured to inspect a wafer.

The system includes an illumination subsystem configured to direct light to the wafer. The illumination subsystem may include a light source such as light source 10 shown in FIG. 1. The light source ma include any suitable light source such as a laser. In this manner, one method to inspect defects may include irradiating a laser beam on an object under inspection. As shown in FIG. 1, the light source may be configured to direct light to wafer 12. However, the illumination subsystem may also include one or more optical elements (not shown) such as mirrors, polarizers, beam splitters, lenses, and the like that are configured to direct light from light source 10 to wafer 12. As shown in FIG. 1, the illumination subsystem may be configured to direct the light to the wafer at an oblique angle of incidence. However, the illumination subsystem may be configured to direct the light to the wafer at any suitable angle(s) of incidence.

The system also includes an image sensor configured to detect light scattered from wafer defects and to generate output responsive to the scattered light. In this manner, the inspection system may use an image sensor to detect the light that a defect scatters. For example, as shown in FIG. 1, light scattered from wafer defects may be collected by lens 14 and directed by the lens to image sensor 16. The lens may include any suitable refractive optical element. However, the lens may also include one or more refractive optical elements and/or one or more reflective optical elements. The system may also include any other suitable optical elements (not shown) such as filters, polarizing elements, and the like positioned in the path of the light scattered from the wafer defects. The lens and/or the system may be configured to collect the light scattered from the wafer defects at any suitable angles (polar and azimuthal). The output generated by the image sensor may include any suitable output such as image signals or data. In one embodiment, the image sensor is a CCD or CMOS sensor.

Figure 2:
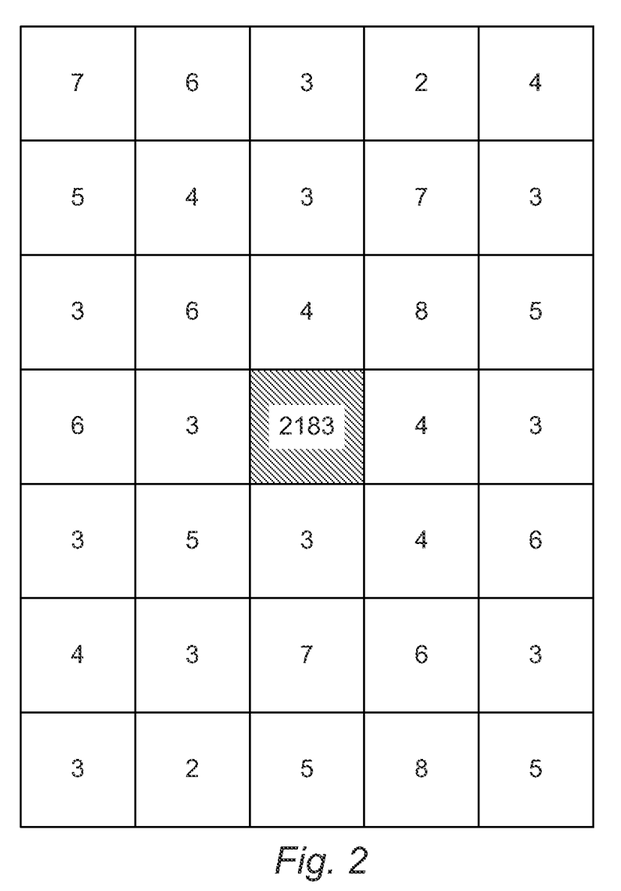
FIG. 2 is a schematic diagram illustrating a plan view of one example of charges detected by pixels of an image sensor, which has an anti-blooming feature, during detection of a defect on a wafer.

The image sensor is configured to not have an anti-blooming feature such that when a pixel in the image sensor reaches full well capacity, excess charge flows from the pixel to one or more neighboring pixels in the image sensor. In this manner, the embodiments described herein are different than other methods for defect inspection which use anti-blooming image sensors. FIG. 2 shows pixels of an anti-blooming image sensor with the center pixel detecting a defect. The numbers shown in FIG. 2 are the counts detected by each of the pixels. FIG. 2 shows that the center pixel of the image sensor detects a defect while the other pixels only receive noise light.

For a 12 bit image sensor, for example, a pixel can detect light with the range of 0 to about 4095 counts. This corresponds to a substantially limited defect size range since the quantity of scattering light is proportional to the sixth power of the defect size. For defects bigger than the maximum range, the excess charge beyond the full well capacity is drained out by the anti-blooming feature. For an image sensor without an anti-blooming feature, when the charge in a pixel exceeds the full well capacity, the charge starts to fill adjacent pixels.

Figure 3:
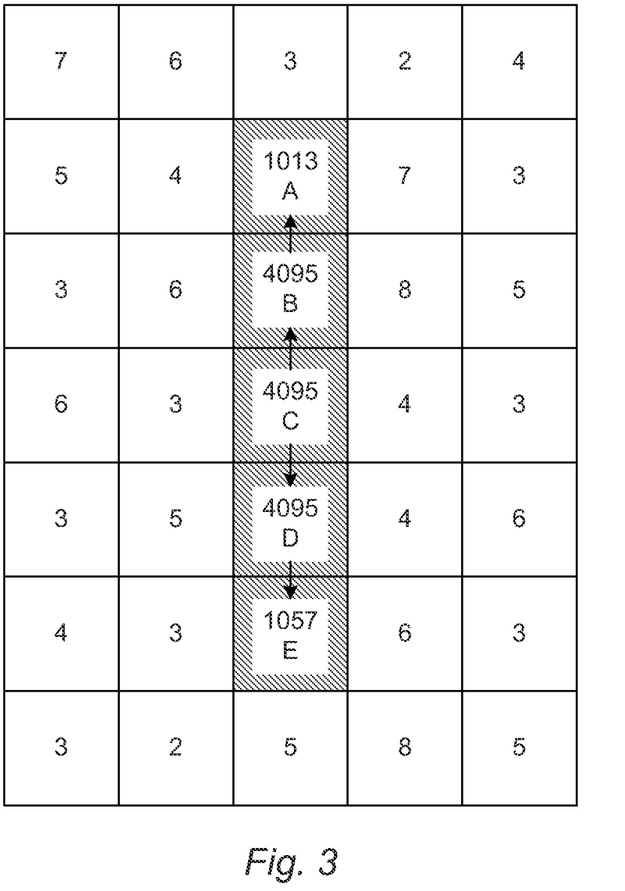
FIG. 3 is a schematic diagram illustrating a plan view of one example of charges detected by pixels of an image sensor that does not have an anti-blooming feature during detection of a defect on a wafer.

In one embodiment, the one or more neighboring pixels include only pixels in one dimension across the image sensor. For example, image sensors can be designed to allow easy vertical shifting of the charge, but potential barriers can be created to reduce flow into horizontal pixels. Hence, the excess charge will preferentially flow into the nearest vertical neighbors. In one such example, FIG. 3 shows that, when the center pixel C detects a defect, the scattering light charges that pixel until its full well capacity of 4095 ADC counts and then the excess charge starts to flow from pixel C to till the vertically adjacent pixels B and D. When pixels B and D also reach the full well capacity, the excess charge starts to flow from pixel C to pixels A and E (through pixels B and D, respectively). Therefore, FIG. 3 shows vertical blooming when only the center pixel receives excess exposure.

Figure 4:
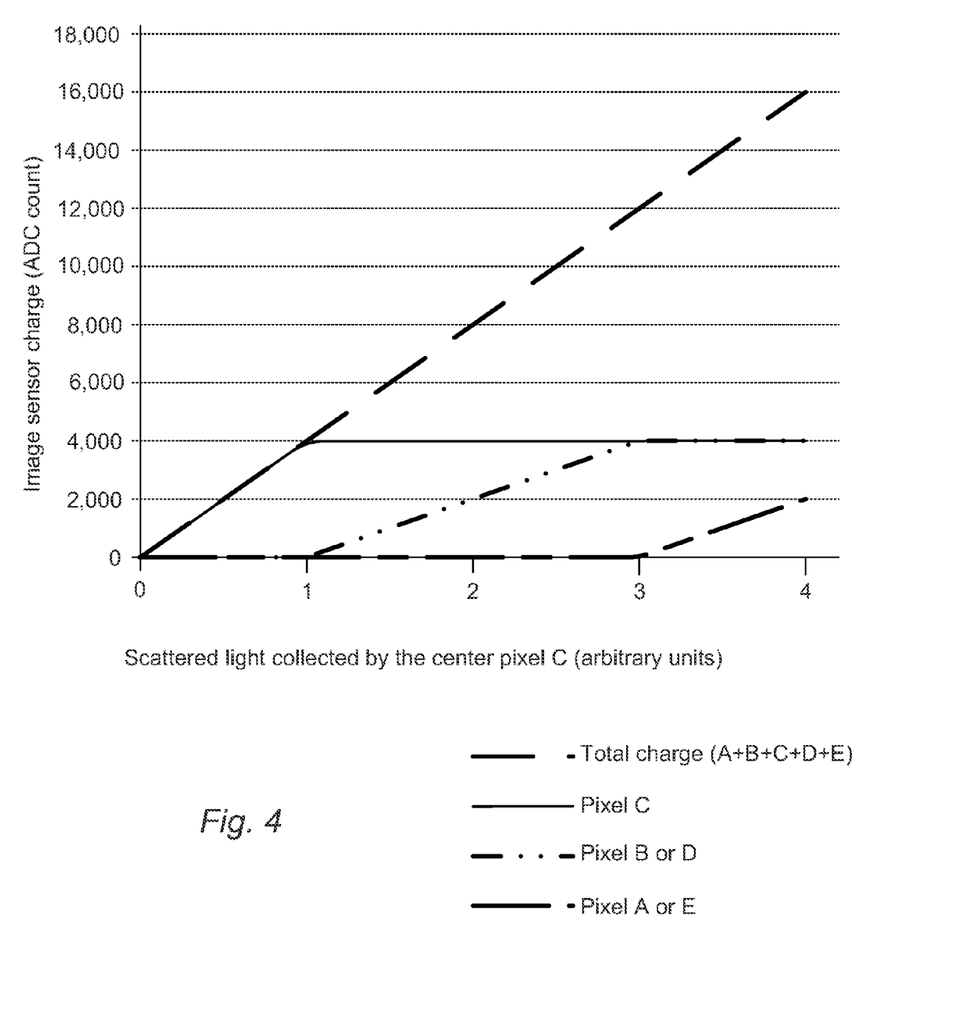
FIG. 4 is a plot showing charge detected by different pixels of an image sensor and a combination of the different pixels as a function of scattered light collected by a center pixel of the image sensor during detection of a defect on a wafer.

In this manner, as shown in FIG. 4, the scattering light collected by the center pixel C shown in FIG. 3 will increase up to arbitrary unit 1 and then level off because the pixel becomes saturated. At that point, the scattering light collected by pixels B and shown in FIG. 3 will as shown in FIG. 4 increase up to arbitrary unit 3 and then level off because the pixels have become saturated. At that point, the scattering light collected by pixels A and E shown in FIG. 3 will as shown in FIG. 4 increase and will eventually level off if those pixels become saturated. In addition, as shown in FIG. 4, the total charge on the combination of all the pixels (A+B+C+D+E) from which and to which excess charge flows will increase as the charge flows between the pixels.

Figure 5:
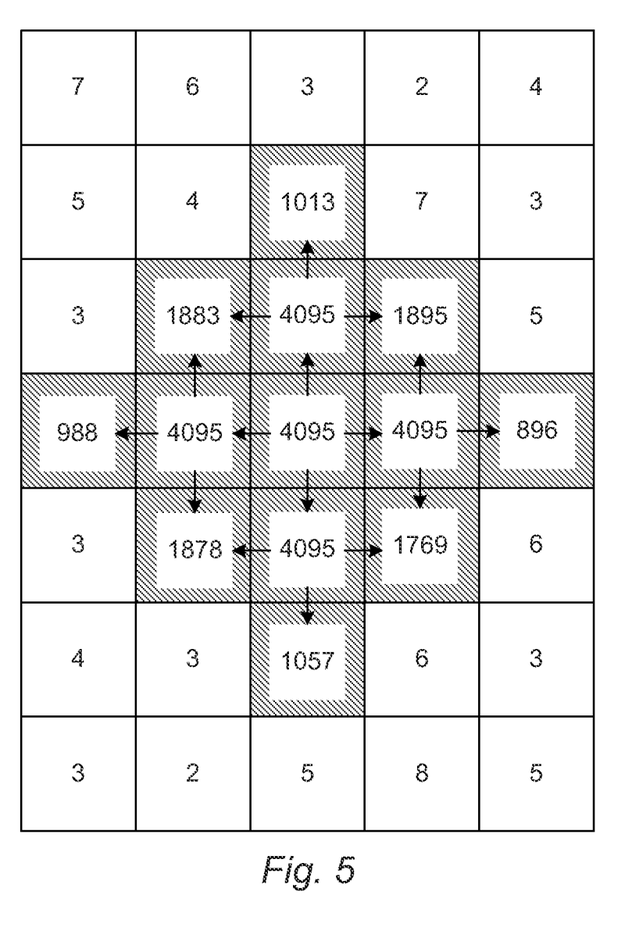
FIG. 5 is a schematic diagram illustrating a plan view of one example of charges detected by pixels of an image sensor that does not have an anti-blooming feature during detection of a defect on a wafer.

In an additional embodiment, the one or more neighboring pixels include pixels in two dimensions across the image sensor. For example, a custom image sensor can be designed to have approximately the same potential barrier in both horizontal and vertical directions, so that the blooming charge can flow into both horizontal and vertical neighbors, as shown in FIG. 5. In some embodiments, the image sensor is configured to have substantially equal blooming in two dimensions. For example, the image sensor shown in FIG. 5 is one example of a custom image sensor designed to have substantially equal blooming in both directions.

In another embodiment, the image sensor is configured to not have the anti-blooming feature across only a portion of the total pixels of the image sensor such that the excess charge of the pixel can only flow to the one or more neighboring pixels within the portion of the total pixels and cannot flow to the one or more neighboring pixels outside of the portion of the total pixels. For example, the image sensor could have anti-blooming only along borders of square or rectangular blocks of pixels (compared with regular anti-blooming image sensors, in which each pixel is anti-blooming). In this way, the blooming will be limited within the blocks (to the extent of the anti-blooming capability), and the size of the blocks in number of pixels can be selected as a trade-off between extended dynamic range and the capability of detecting more defects other than the one that otherwise could cause blooming out of the block within the same frame. For example, a 2,000×1,000 pixel image sensor could be divided into 50 blocks with each block having 200×200 pixels. Only the pixels along the border of the 200×200 pixel blocks are designed to have the anti-blooming feature while the other pixels do not. In this example, the blooming calibration will extend the dynamic range by about 200×200 times while the blooming will be limited to each block by anti-blooming along each of the block's borders.

In one embodiment, the system is configured to calibrate the image sensor for variations in the flow of the excess charge from the pixel to the one or more neighboring pixels. For example, because the blooming would not be perfect and some charges could get lost, as well as the charge conversion (to voltage) would not be perfectly linear up to the full well depth of a pixel, in reality the total charge detected directly in ADC counts would not be perfectly linear as shown in FIG. 4. Therefore, the nonlinearity can be calibrated out to know more accurately the total charge based on the ADC counts. The calibration of all the blooming pixel charge extends the measurement range of the defect size, by the times of the number of the blooming pixels, which is up to the image sensor pixel number. The computer subsystem described further herein may be used by the system to perform the calibration described above.

The system further includes a computer subsystem configured to detect the defects on the wafer using the output and to determine a size of the defects on the wafer using the output generated by a pixel and any neighboring pixels of the pixel to which the excess charge of the pixel flows. For example, as shown in FIG. 1, the system may include computer subsystem 18 configured to detect defects on the wafer using output of image sensor 16. The computer subsystem may take various forms, including a personal computer system, image computer, mainframe computer system, workstation, network appliance, Internet appliance, or other device. In general, the term "computer subsystem" may be broadly defined to encompass any device having one or more processors, which executes instructions from a memory medium. The computer subsystem may also include any suitable processor known in the art such as a parallel processor. In addition, the computer subsystem may include a computer platform with high speed processing and software, either as a standalone or a networked tool.

The computer subsystem may be configured to detect the defects on the wafer using the output and any suitable defect detection method and/or algorithm. The defect size may be measured based on the amount of light that it scatters. The computer subsystem described herein would determine defect size differently than the computer subsystems of other inspection systems. For example, the computer subsystem would determine the defect size based on the total charge of the whole blooming area of the image sensor. For example, in one embodiment, the computer subsystem is configured to determine the size of the defects by adding the charges of the pixel and any neighboring pixels to which the excess charge of the pixel flows to determine a total charge and determining the size from the total charge in the example shown in FIG. 3 described above, although pixel C saturates at 4095 ADC counts, which corresponds to a portion of the total scattering light of the defect, the total charge of pixels A, B, C, D, and F, which is 14,355, measures the total scattering light. Therefore, unlike other computer subsystems, which would determine the defect size based just on the 4095 ADC counts detected by pixel C, the computer subsystem described herein would determine the detect size based on the total charge of pixels A, B, C, D, and E, which is 14,355. The computer subsystem described herein may also be different than the computer subsystems of other inspection systems in that the computer subsystem may be configured to calibrate the blooming as described above.

In one embodiment, the system has a detect size range that is greater than if the computer subsystem used output generated by an image sensor that does have the anti-blooming feature to determine the size of the defects. For example, as described herein, the embodiments may use a blooming calibration to extend the sizing range of defect inspection. In addition, a custom image sensor with substantially equal blooming in both horizontal and vertical directions can be used to extend the sizing range more significantly, for example, by 10,000 times with a circle blooming of 113 pixel diameter. Furthermore, the embodiments described herein can also be used for other applications that detect any feature instead of just a defect where the measurement range of total light is more important than the pixel to pixel spatial resolution.

In some embodiments, the system includes an additional detector configured to detect other light scattered from the wafer defects (e.g., from different angles as the image sensor or the same angles as the image sensor by using a beam splitter (not shown) to detect a fraction of the scattering light that the image sensor detects) and to generate additional output responsive to the other scattered light. The additional detector is not an image sensor that does not have an anti-blooming feature. The computer subsystem is configured to detect the defects on the wafer using the additional output and to determine if multiple defects correspond to the output generated by the pixel and any neighboring pixels of the pixel to which the excess charge of the pixel flows. For example, as shown in FIG. 1, the system may include additional detector 20 that is configured to detect other light scattered from the wafer defects. For example, additional detector 20 and image sensor 16 are configured to separately detect light that is scattered at different angles from the wafer defects. Therefore, image sensor 16 and additional detector 20 do not detect the same scattered light. The additional detector may include any detector that is not an image sensor that does not have an anti-blooming feature. For example, the additional detector could be a CCD that does have an anti-blooming feature, a multi-anode photomultiplier tube (PMT), and the like.

As also shown in FIG. 1, the system may include lens 22 configured to collect the other light scattered from the wafer defects and to direct the other scattered light to additional detector 20. The lens may include any suitable refractive optical element. However, the lens may also include one or more refractive optical elements and/or one or more reflective optical elements. The system may also include any other suitable optical elements (not shown) such as filters, polarizing elements, and the like positioned in the path of the other light scattered from the wafer defects. The lens and/or the system may be configured to collect the other light scattered from the wafer defects at any suitable angles (polar and azimuthal). The output generated by the additional detector may include any suitable output such as image signals or data. The computer subsystem may be configured to detect the defects on the wafer using the output generated by the additional detector and any suitable defect detection method and/or algorithm.

The additional detector may be used as a channel with regular anti-blooming to determine the number of defects within the area of the blooming pixels of the image sensor described herein. For example, based on information from only one blooming image sensor, multiple defects may not be distinguishable from each other within a whole single blooming area. However, that may be acceptable for many applications. The system may, however, have multiple channels (e.g., defined by image sensor 16 and additional detector 20). Therefore, one of the channels may be used to determine the number of defects within a whole single blooming area. The computer subsystem may be configured to perform such functions in any suitable manner.

Another embodiment relates to a method for inspecting a wafer. The method includes directing light to the wafer, which may be performed as described further herein. The method also includes detecting light scattered from wafer defects and generating output responsive to the scattered light using an image sensor, which may be performed as described herein. The image sensor does not have an anti-blooming feature such that when a pixel in the image sensor reaches full well capacity, excess charge flows from the pixel to one or more neighboring pixels in the image sensor. The image sensor may be further configured as described herein. In addition, the method includes detecting the defects on the wafer using the output, which may be performed as described further herein. The method further includes determining a size of the defects on the wafer using the output generated by a pixel and any neighboring pixels of the pixel to which the excess charge of the pixel flows, which may be performed as described further herein.

In one embodiment, the method includes calibrating the image sensor for variations in the flow of the excess charge from the pixel to the one or more neighboring pixels, which may be performed as described further herein. In another embodiment, the size of the defects is determined in the method with a range that is greater than if the method used output generated by an image sensor that does have the anti-blooming feature to determine the size of the defects. In an additional embodiment, the one or more neighboring pixels include only pixels in one dimension across the image sensor. In a further embodiment, the one or more neighboring pixels include pixels in two dimensions across the image sensor. In another embodiment, the image sensor has substantially equal blooming in two dimensions. In some embodiments, the image sensor does not have the anti-blooming feature across only a portion of the total pixels of the image sensor such that the excess charge of the pixel can only flow to the one or more neighboring pixels within the portion of the total pixels and cannot flow to the one or more neighboring pixels outside of the portion of the total pixels. Such image sensor embodiments may be further configured as described herein.

In one embodiment, determining the size of the defects includes adding the charges of the pixel and any neighboring pixels to which the excess charge of the pixel flows to determine a total charge and determining the size from the total charge, which may be performed as described herein. In another embodiment, the method includes detecting other light scattered from the wafer defects and generating additional output responsive to the other scattered light using an additional detector, which may be performed as described herein. The additional detector is not an image sensor that does not have an anti-blooming feature. The additional detector may be further configured as described herein. The method also includes detecting the defects on the wafer using the additional output and determining if multiple defects correspond to the output generated by the pixel and any neighboring pixels of the pixel to which the excess charge of the pixel flows, which may be performed as described herein. In another embodiment, the image sensor is a CCD or a CMOS sensor.

An additional embodiment relates to a computer-implemented method for determining a size of defects on a wafer. The method includes acquiring output of an image sensor included in an inspection system. The output is generated by directing light to the wafer and detecting light scattered from wafer defects, which may be performed as described herein. Acquiring the output may include using an inspection system to acquire the output, for example, by scanning the wafer with light and detecting light scattered from the wafer defects. In this manner, acquiring the output may include performing an inspection of the wafer. The inspection system may be configured as described herein. Alternatively, acquiring the output may include acquiring the output from an inspection system used to generate the output. For example, the method may include acquiring the output from a storage medium in which the inspection system stored the output. The storage medium may include a storage medium of the inspection system, a fab database, or any other suitable storage medium known in the art. In this manner, acquiring the output may not include inspecting the wafer.

The image sensor is configured to not have an anti-blooming feature such that when a pixel in the image sensor reaches full well capacity, excess charge flows from the pixel to one or more neighboring pixels in the image sensor. The method also includes using a computer system to detect the defects on the wafer using the output and to determine a size of the defects on the wafer using the output generated by a pixel and any neighboring pixels of the pixel to which the excess charge of the pixel flows, which may be performed as described herein. The computer system may be further configured as described herein with respect to a computer subsystem.

In one embodiment, the method includes using the computer system to calibrate the image sensor for variations in the flow of the excess charge from the pixel to the one or more neighboring pixels, which may be performed as described herein. In another embodiment, using the computer system to determine the size of the defects includes adding the charges of the pixel and any neighboring pixels to which the excess charge of the pixel flows to determine a total charge and determining the size from the total charge, which may be performed as described further herein. In an additional embodiment, the method includes acquiring additional output that is generated by using an additional detector included in the inspection system to detect other light scattered from the wafer and to generate the additional output responsive to the other scattered light, which may be performed as described herein. The additional detector is not an image sensor that does not have an anti-blooming feature. The additional detector may be further configured as described herein. The method also includes using the computer system to detect the defects on the wafer using the additional output and to determine if multiple defects correspond to the output generated by the pixel and any neighboring pixels of the pixel to which the excess charge of the pixel flows, which may be performed as described herein.

Each of the embodiments of the methods described above may include any other step(s) of any other method(s) described herein. Furthermore, each of the embodiments of the methods described above may be performed by any of the systems described herein.

All of the methods described herein may include storing results of one or more steps of the method embodiments in a storage medium. The results may include any of the results described herein and may be stored in any manner known in the art. The storage medium may include any suitable computer-readable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

In contrast to the embodiments described herein, the total drained charge through an anti-blooming structure using an anti-blooming image sensor may be measured and used to determine defect size. However, such a configuration would require extra circuitries and cannot distinguish multiple defects within the same image sensor frame.

Further modifications and alternative embodiments of various aspects of the invention may be apparent to those skilled in the art in view of this description. For example, various embodiments for extended defect sizing range for wafer inspection are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to inspect a wafer, comprising:
   an illumination subsystem configured to direct light to the wafer;
   an image sensor configured to detect light scattered from wafer defects and to generate output responsive to the scattered light, wherein the image sensor is further configured to not have an anti-blooming feature such that when a pixel in the image sensor reaches full well capacity, excess charge flows from the pixel to one or more neighboring pixels in the image sensor; and
   a computer subsystem configured to detect the defects on the wafer using the output and to determine a size of the defects on the wafer using the output generated by a pixel and any neighboring pixels of the pixel to which the excess charge of the pixel flows, wherein the computer subsystem is further configured to determine the size of the defects by adding charges of the pixel and any neighboring pixels to which the excess charge of the pixel flows to determine a total charge and determining the size from the total charge.

2. The system of claim 1, wherein the system is further configured to calibrate the image sensor for variations in the flow of the excess charge from the pixel to the one or more neighboring pixels.

3. The system of claim 1, wherein the system has a defect size range that is greater than if the computer subsystem used output generated by an image sensor that does have the anti-blooming feature to determine the size of the defects.

4. The system of claim 1, wherein the one or more neighboring pixels comprise only pixels in one dimension across the image sensor.

5. The system of claim 1, wherein the one or more neighboring pixels comprise pixels in two dimensions across the image sensor.

6. The system of claim 1, wherein the image sensor is further configured to have substantially equal blooming in two dimensions.

7. The system of claim 1, wherein the image sensor is further configured to not have the anti-blooming feature across only a portion of the total pixels of the image sensor such that the excess charge of the pixel can only flow to the one or more neighboring pixels within the portion of the total pixels and cannot flow to the one or more neighboring pixels outside of the portion of the total pixels.

8. The system of claim 1, further comprising an additional detector configured to detect other light scattered from the wafer defects and to generate additional output responsive to the other scattered light, wherein the additional detector is not an image sensor that does not have an anti-blooming feature, and wherein the computer subsystem is further configured to detect defects on the wafer using the additional output and to determine if multiple defects correspond to the output generated by the pixel and any neighboring pixels of the pixel to which the excess charge of the pixel flows.

9. The system of claim 1, wherein the image sensor is a charge coupled device or a CMOS sensor.

10. A method for inspecting a wafer, comprising:
    directing light to the wafer;
    detecting light scattered from wafer defects and generating output responsive to the scattered light using an image sensor, wherein the image sensor does not have an anti-blooming feature such that when a pixel in the image sensor reaches full well capacity, excess charge flows from the pixel to one or more neighboring pixels in the image sensor;
    detecting defects on the wafer using the output; and
    determining a size of the defects on the wafer using the output generated by a pixel and any neighboring pixels of the pixel to which the excess charge of the pixel flows, wherein determining the size of the defects comprises adding charges of the pixel and any neighboring pixels to which the excess charge of the pixel flows to determine a total charge and determining the size from the total charge, and wherein said detecting the defects and said determining are performed by a computer system.

11. The method of claim 10, further comprising calibrating the image sensor for variations in the flow of the excess charge from the pixel to the one or more neighboring pixels.

12. The method of claim 10, wherein the size of the defects is determined in the method with a range that is greater than if the method used output generated by an image sensor that does have the anti-blooming feature to determine the size of the defects.

13. The method of claim 10, wherein the one or more neighboring pixels comprise only pixels in one dimension across the image sensor.

14. The method of claim 10, wherein the one or more neighboring pixels comprise pixels in two dimensions across the image sensor.

15. The method of claim 10, wherein the image sensor has substantially equal blooming in two dimensions.

16. The method of claim 10, wherein the image sensor does not have the anti-blooming feature across only a portion of the total pixels of the image sensor such that the excess charge of the pixel can only flow to the one or more neighboring pixels within the portion of the total pixels and cannot flow to the one or more neighboring pixels outside of the portion of the total pixels.

17. The method of claim 10, further comprising detecting other light scattered from the wafer defects and generating additional output responsive to the other scattered light using an additional detector, wherein the additional detector is not an image sensor that does not have an anti-blooming feature, and further comprising detecting defects on the wafer using the additional output and determining if multiple defects correspond to the output generated by the pixel and any neighboring pixels of the pixel to which the excess charge of the pixel flows.

18. The method of claim 10, wherein the image sensor is a charge coupled device or a CMOS sensor.

19. A computer-implemented method for determining a size of defects on a wafer, comprising:

acquiring output of an image sensor included in an inspection system, wherein the output is generated by directing light to the wafer and detecting light scattered from wafer defects, and wherein the image sensor is configured to not have an anti-blooming feature such that when a pixel in the image sensor reaches full well capacity, excess charge flows from the pixel to one or more neighboring pixels in the image sensor; and detecting the defects on the wafer using the output and determining a size of the defects on the wafer using the output generated by a pixel and any neighboring pixels of the pixel to which the excess charge of the pixel flows, wherein determining the size of the defects comprises adding charges of the pixel and any neighboring pixels to which the excess charge of the pixel flows to determine a total charge and determining the size from the total charge, and wherein said acquiring, said detecting, and said determining are performed by a computer system.

20. The method of claim 19, further comprising calibrating the image sensor for variations in the flow of the excess charge from the pixel to the one or more neighboring pixels with the computer system.

21. The method of claim 19, further comprising acquiring additional output that is generated by using an additional detector included in the inspection system to detect other light scattered from the wafer defects and to generate the additional output responsive to the other scattered light, wherein the additional detector is not an image sensor that does not have an anti-blooming feature, and further comprising detecting the defects on the wafer using the additional output and determining if multiple defects correspond to the output generated by the pixel and any neighboring pixels of the pixel to which the excess charge of the pixel flows, wherein detecting the defects using the additional output and determining if the multiple defects correspond to the output are performed by the computer system.

\* \* \* \* \*